US00PP15090P2

(12) United States Plant Patent
Ault

(10) Patent No.: US PP15,090 P2
(45) Date of Patent: Aug. 17, 2004

(54) ECHINACEA PLANT NAMED 'ART'S PRIDE'

(50) Latin Name: *Echinacea hybrida*
Varietal Denomination: Art's Pride

(75) Inventor: James R. Ault, Glencoe, IL (US)

(73) Assignee: Chicagoland Grows, Inc., Glencoe, IL (US)

( * ) Notice: Subject to any disclaimer, the term of this patent is extended or adjusted under 35 U.S.C. 154(b) by 12 days.

(21) Appl. No.: 10/680,132

(22) Filed: Oct. 8, 2003

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

A new and distinct highly ornamental Echinacea plant is provided. The blossoms are attractive and display orange-colored ray florets. A sweet orange-spiced tea fragrance emanates from the blossoms. Semi-glossy green foliage is formed that contrasts nicely with the blossom coloration. The plant is free-flowering and commonly blooms from early-July to mid- to late-August at Glencoe, Ill., U.S.A.

4 Drawing Sheets

Botanical/commercial classification: *Echinacea hybrida*/ Echinacea Plant.
Varietal denomination: cv. 'Art's Pride'.

SUMMARY OF THE INVENTION

The invention relates to a new and distinct Echinacea plant that was the product of a controlled breeding program that was conducted at the Chicago Botanic Garden located at Glencoe, Ill., U.S.A.

The female parent (i.e., seed parent) was *Echinacea purpurea* 'Alba' (non-patented in the United States), and the male parent (i.e., pollen parent) was an unnamed seedling of *Echinacea paradoxa* (non-patented in the United States). The 'Alba' female parent was produced by the crossing of two seed grown plants of *Echinacea purpurea* 'White Swan' (non-patented in the United States). The parentage of the new cultivar can be summarized as follows:

*Echinacea purpurea* 'Alba'×*Echinacea paradoxa* (Unnamed Seedling).

The seeds resulting from the above pollination were sown and small plants were obtained which were physically and biologically different from each other. Selective study resulted in the identification of a single plant of the new cultivar.

It was found that the new Echinacea cultivar of the present invention possesses the following combination of characteristics:

(a) forms attractive blossoms having orange-colored ray florets, (b) displays a blossom fragrance of sweet orange-spiced tea, and (c) forms attractive semi-glossy green foliage that contrasts nicely with the blossom coloration.

The new cultivar can be readily distinguished from its parental plants by the distinctive orange coloration of the ray florets and the distinctive fragrance of the blossoms. Plants of the *paradoxa* species are known to display yellow ray florets, a different blossom fragrance, and a different growth habit.

The new cultivar is well suited for growing as attractive colorful ornamentation in gardens and in the landscape.

Asexual reproduction of the new cultivar by tissue culture was first conducted at Glencoe, Ill., U.S.A. during 2002. Root cuttings and division also has been used to asexually propagate the new cultivar at the some location. The asexual reproduction has demonstrated that the unique combination of characteristics of the new cultivar is firmly fixed and is well retained through successive generations of asexual propagation. Accordingly, the new cultivar asexually reproduces true to type. When cuttings are utilized to reproduce the new cultivar, a well rooted plant commonly is formed in approximately 10 to 12 weeks.

The new cultivar has been named 'Art's Pride'.

BRIEF DESCRIPTION OF THE PHOTOGRAPHS

The accompanying photographs show as true as it is reasonably possible to make the same in color illustrations of this character typical plants and plant parts of the new cultivar of the present invention. Please refer to The R.H.S. Colour Chart information expressed hereafter for a more precise specification of color. The depicted plants were approximately two years of age and were growing outdoors under full sun during July at Glencoe, Ill., U.S.A.

DETAILED DESCRIPTION

Figure 1:
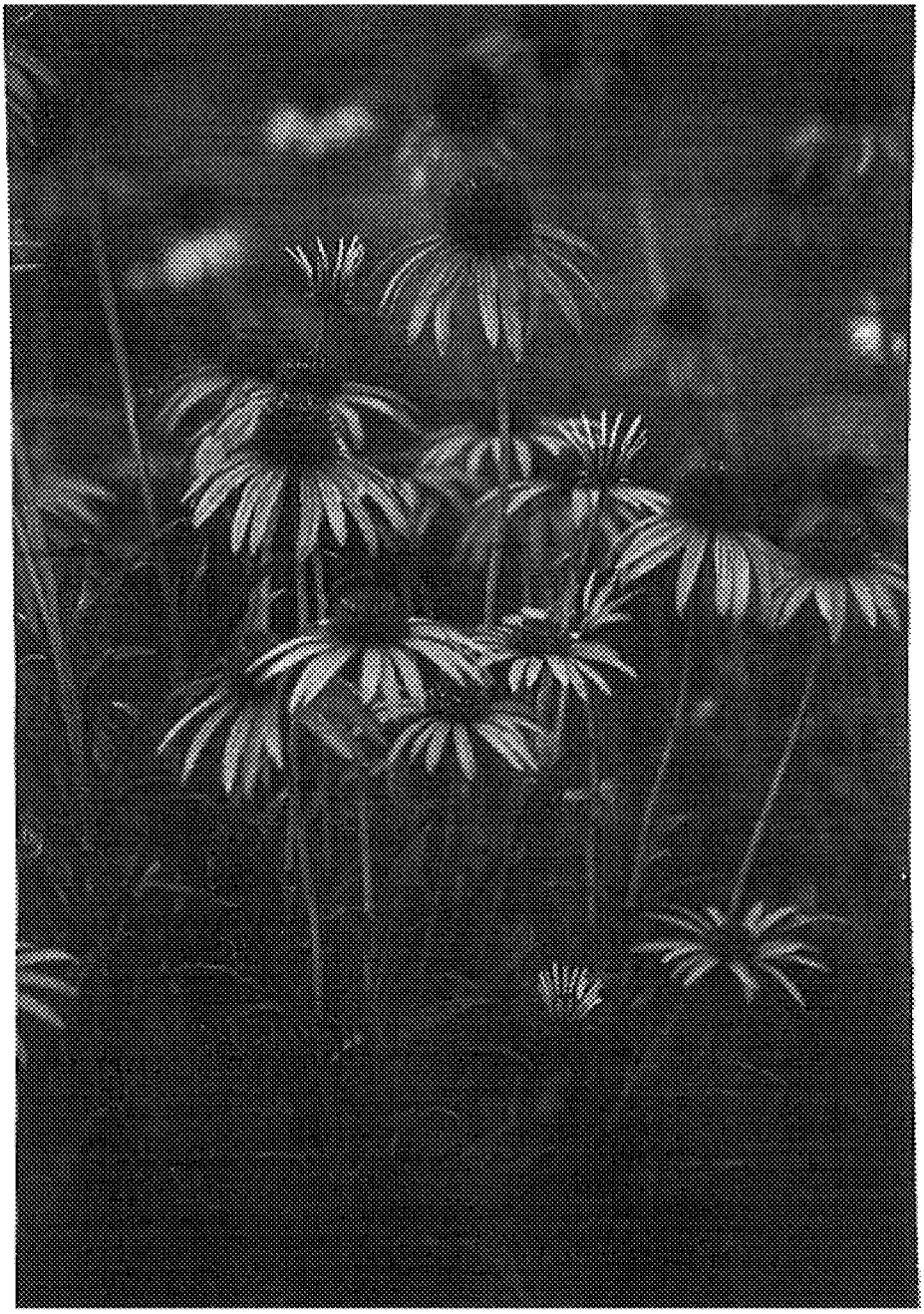
FIG. 1 shows an overall view of plant while growing in a field setting.
Figure 2:
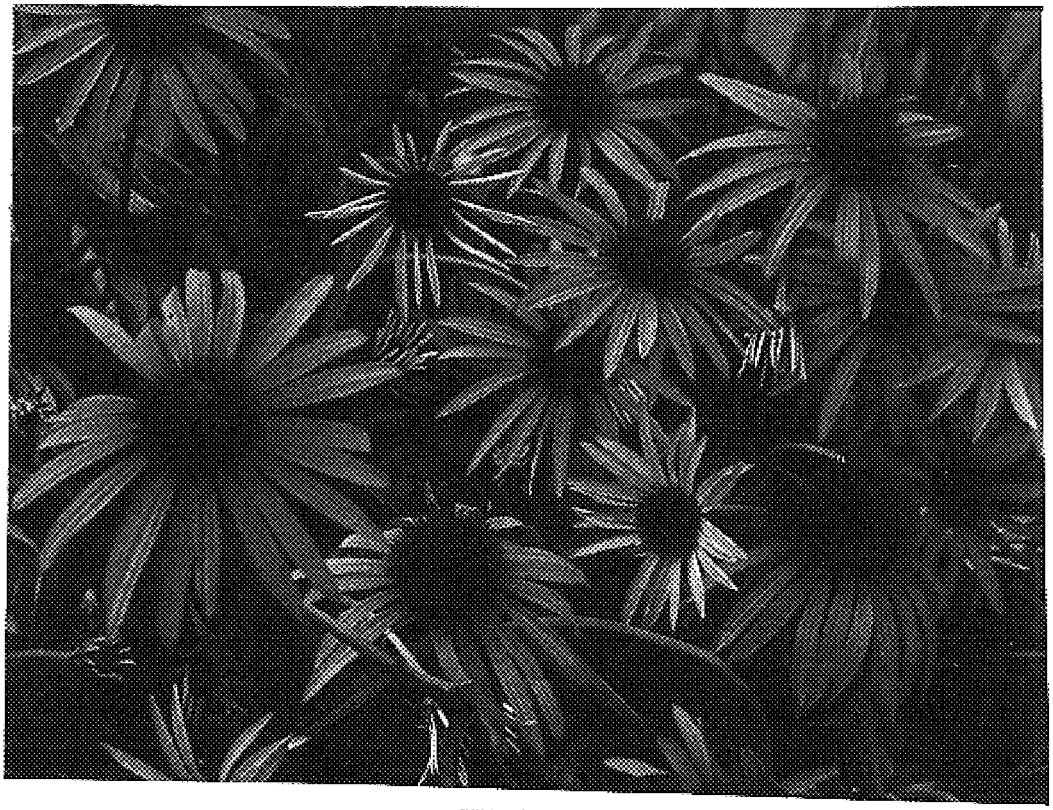
FIG. 2 shows a closer view of inflorescence in various stages of maturation.
Figures 3, 4, 9, 10, 11, 13:
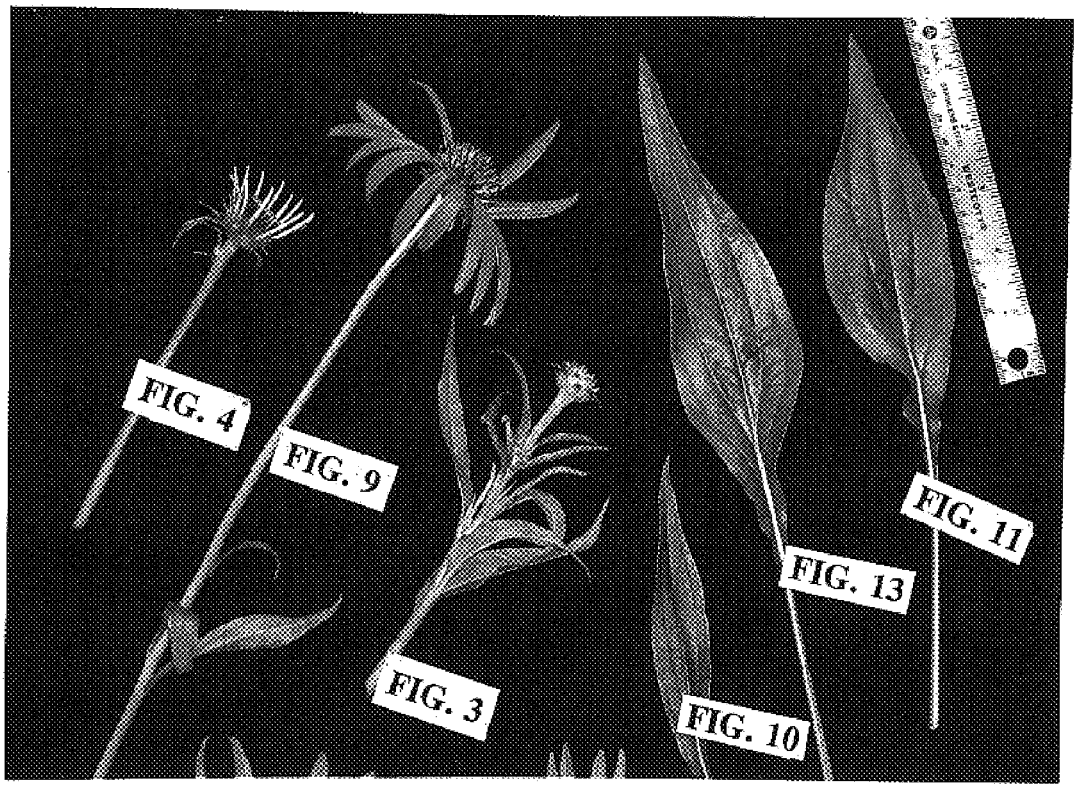
FIG. 3 shows an unopened bud and young foliage.
FIG. 4 shows a bud in the course of opening with emerging ray florets.
FIG. 9 shows a side view of a mature inflorescence.
FIG. 10 shows an immature sessile leaf from above the basal area of the stem—plan view—obverse.
FIG. 11 shows a basal petiolate leaf—plan view—obverse. Dimensions in centimeters and inches are included to the right of the leaf.
FIG. 13 shows a further basal petiolate leaf—plan view—obverse. It will be noted that the shape varies somewhat from the leaf of FIG. 11.
Figures 5, 6, 7, 8, 12:
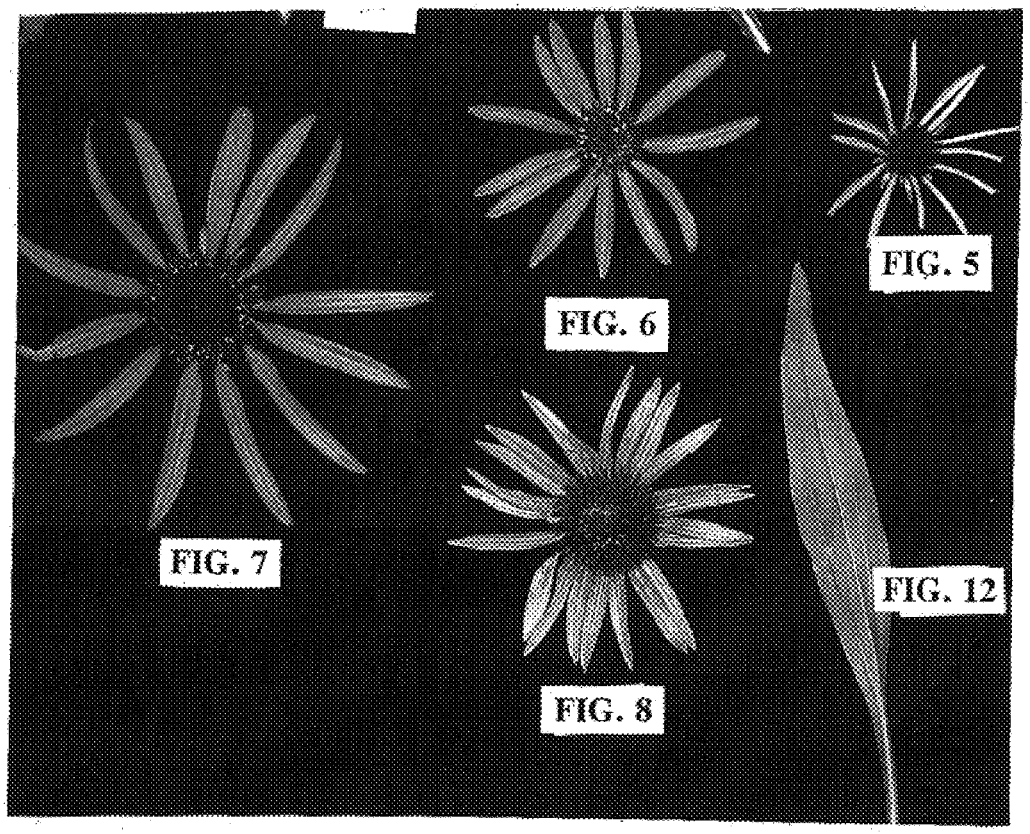
FIG. 5 shows a newly-opened inflorescence—plan view—obverse.
FIG. 6 shows an inflorescence of intermediate maturity—plan view—obverse.
FIG. 7 shows a mature inflorescence—plan view—obverse.
FIG. 8 shows an aging inflorescence—plan view—obverse.
FIG. 12 shows a sessile leaf occurring near the top of a stem—plan view—obverse.

The following description is based upon the observation of two year-old plants of the new cultivar while growing in an outdoor garden during July under full sun conditions at Glencoe, Ill., U.S.A. The chart used in the identification of the colors is The R.H.S. Colour Chart of The Royal Horticultural Society, London, England.

Plant:

*Height.*—Approximately 70 to 80 cm.

*Width.*—Approximately 60 to 80 cm.

*Lateral branches.*—Length: Approximately 5 to 22 cm. Diameter: Approximately 0.3 to 0.5 cm. Internode length: Approximately 3 to 15 cm. Aspect: Mostly upright. Texture: Roughly strigose pubescent. Color: Yellow-Green Group 150C.

Foliage:

*Arrangement.*—Alternate, single.

*Mature length.*—Approximately 22 cm on average.

*Mature width.*—Approximately 5 cm at the widest point.

*Shape.*—Narrowly lanceolate, petiolate below, and becoming reduced and sessile at upper locations.

*Apex.*—Acute.

*Base.*—Cuneate.

*Margin.*—Entire to remotely serrated, and undulate (as illustrated in the photographs).

*Venation pattern.*—Pinnate and predominantly three-veined.

*Texture.*—Somewhat rough and pubescent on both surfaces.

*Color.*—Immature leaf: Upper surface: commonly between Green Group 137C and Yellow-Green Group 147B. Under surface: Green Group 138A. Mature leaf: Upper surface: commonly between Green Group 137C and 138A. Under surface: Green Group 137C. Immature petiole: Yellow-Green Group 145B commonly with striations of Yellow-Green Group 144B. Mature petiole: Yellow-Green Group 145A commonly with striations of Yellow-Green Group 144B. Venation: Yellow-Green Group 145B on the upper surface.

Inflorescence:

*Type.*—Capitulum.

*Description.*—Borne upright singly both terminal and axillary on long stout pedicels. The heads are radially symmetrical. Involucre bracts (phyllaries) located below the ray florets are foliaceous, imbricate, lanceolate, and in three series. The ray florets are present in a single series, are sterile, and each possess a single elongated ligule. The disk florets are fertile, are spirally arranged on a conical receptacle, and are individually subtended by chaffy bracts (pales). The pales terminate in a condupliate smooth pointed spine exceeding the length of the disc florets. The heads are persistent.

*Flowering time.*—Continuously and freely commonly from early-July to mid- to late-August.

*Longevity.*—Good color and flower form commonly last approximately 7 to 10 days on the plant, and approximately 5 days when cut and placed in a vase.

*Quantity.*—Free-flowering with approximately 12 to 18 open inflorescences being present on a plant at one time.

*Fragrance.*—Strong, as sweet orange-spiced tea.

*Buds.*—Shape: ovoid when closed. Diameter: approximately 1 to 1.8 cm on average. Color: commonly between Yellow-Green Group 144A and 145A.

*Flower diameter.*—Approximately 1.5 to 2 cm when ray floret coloration first shows, and approximately 12 cm when fully expanded.

*Ray florets.*—Color: Mixture of Orange Group 24A and 26A when color begins to appear, a mixture of Orange Group 28A and 28B on the upper surface during the course of opening, Yellow-Orange Group 22C on the under surface during the course of opening, a mixture of Orange-Red Group 31A and 32A on the upper surface when fully expanded, and Red Group 51C with highlights of Red Group 51A on the under surface when fully expanded. Length: Approximately 5.5 cm on average. Width: Approximately 1.1 cm on average at the widest point. Shape: Narrowly oblanceolate. Number: Commonly approximately 12 to 18 with a long persistence. Apex: Emarginate and bifid. Base: Acute. Margin: Entire. Texture: Smooth. Orientation: Initially substantially horizontal, and upon maturity commonly droop approximately 30° to 45° from the horizontal towards the peduncle.

*Disc florets.*—Color: Mixture of Greyed-Orange Group 167D, Greyed-Red Group 178A, and Greyed-Purple Group 185A during the course of opening; and a mixture of Greyed-Red Group 178A, Greyed-Red Group 179B, Greyed-Purple Group 185A, and Greyed-Purple Group 187B when fully expanded. Length: Approximately 0.4 to 0.5 cm on average. Width: Approximately 0.2 cm on average. Shape: Tubular and elongated. Apex: Five-lobed with acute points.

*Phyllaries.*—Length: Approximately 0.7 to 1.4 cm on average. Diameter: Approximately 0.3 to 0.4 cm on average. Shape: Lanceolate and reflexed. Apex: Narrowly acute. Base: Fused. Margin: Entire and strigose pubescent. Texture: Smooth. Number: Approximately 38 on average.

*Pales.*—Length: Approximately 1.5 to 1.7 cm in total, and commonly extend approximately 0.9 to 1.1 cm above the receptacle. Diameter: Approximately 0.1 cm. Shape: Awl-shaped. Apex: Pointed and incurved. Texture: Smooth. Color: Yellow-Green Group 144A at the base, Greyed-Red Group 180A at the middle, and Greyed-Purple Group 183A at the tip.

*Peduncles.*—Length: Approximately 20 cm on average. Diameter: Approximately 0.3 to 0.5 cm on average. Disposition: Mostly substantially erect. Strength: Relatively strong. Texture: Pubescent. Color: Yellow-Green Group 145B commonly with striations of Yellow-Green Group 145A.

*Androecium.*—Location: Present only in disc florets. Stamen number: Five per flower. Pollen: Yellow-Orange Group 15A in coloration.

*Gynoecium.*—Location: Present only in disc florets. Pistil number: One. Pistil length: Approximately 0.7 to 0.9 cm on average. Style length: Approximately 0.1 to 0.2 cm. Stigma: Substantially round in cross-section.

*Fruit.*—Type: Cypselae (achene). Quantity: One per inflorescence. Length: Approximately 0.4 to 0.6 cm. Shape: Substantially quadrangular. Size: Approximately 0.3 cm across at distal end. Color: Brown Group 200A with some stripes of Grey-Brown Group 199A.

*Seeds.*—Quantity: One per fruit. Length: Approximately 0.3 to 0.4 cm. Diameter: Approximately 0.2 cm. Color: Orange-White Group 159A with a base of Greyed-Orange Group 164A.

No particular resistance to pathogens and pests commonly encountered with Echinacea plants has been noted to date when observing plants of the new cultivar being grown at Glencoe, Ill., U.S.A.

The new cultivar of the present invention has withstood temperatures as low as −15° F. and has tolerated temperatures as high as 100° F.

The new cultivar has not been observed to data under all possible environmental conditions. Accordingly, it is possible that the phenotype may vary somewhat with variations in the environment, such as temperature, light intensity, day length, and other cultural conditions without variance of the genotype.

I claim:

1. A new and distinct Echinacea plant having the following combination of characteristics:

(a) forms attractive blossoms having orange-colored ray florets, (b) displays a blossom fragrance of sweet orange-spiced tea, and (c) forms attractive semi-glossy green foliage that contrasts nicely with the blossom coloration;

substantially as illustrated and described.

* * * * *